(12) United States Patent
Nakamura et al.

(10) Patent No.: US 7,655,449 B2
(45) Date of Patent: Feb. 2, 2010

(54) β-FRUCTOFURANOSIDASE VARIANTS

(75) Inventors: Hirofumi Nakamura, Sakado (JP);
Akitaka Nakane, Sakado (JP);
Hidetoshi Kubota, Sakado (JP)

(73) Assignee: Meiji Seika Kaisha Ltd., Tokyo (JP)

( * ) Notice: Subject to any disclaimer, the term of this patent is extended or adjusted under 35 U.S.C. 154(b) by 262 days.

(21) Appl. No.: 10/591,751

(22) PCT Filed: Mar. 4, 2005

(86) PCT No.: PCT/JP2005/003787

§ 371 (c)(1),
(2), (4) Date: Sep. 1, 2006

(87) PCT Pub. No.: WO2005/085447

PCT Pub. Date: Sep. 15, 2005

(65) Prior Publication Data

US 2008/0187970 A1  Aug. 7, 2008

(30) Foreign Application Priority Data

Mar. 4, 2004  (JP) ............................. 2004-060426

(51) Int. Cl.
C12P 19/00 (2006.01)
C12N 9/00 (2006.01)
C12N 9/24 (2006.01)
C12N 9/26 (2006.01)
C12N 1/20 (2006.01)
C12N 15/00 (2006.01)
C07H 21/04 (2006.01)

(52) U.S. Cl. .................. 435/201; 435/72; 435/183; 435/200; 435/252.3; 435/320.1; 536/23.2

(58) Field of Classification Search .................. None
See application file for complete search history.

(56) References Cited

U.S. PATENT DOCUMENTS 6,337,201 B1 * 1/2002 Yanai et al. ................ 435/200
6,566,111 B1   5/2003 Yanai et al.
2002/0192771 A1  12/2002 Yanai et al.

FOREIGN PATENT DOCUMENTS

| EP | 0 889 134 | 1/1999 |
|---|---|---|
| EP | 1 022 332 | 7/2000 |
| JP | 2004-242528 | 9/2004 |
| WO | 97/34004 | 9/1997 |
| WO | 99/13059 | 3/1999 |
| WO | 2004/078966 | 9/2004 |

OTHER PUBLICATIONS

Kaper et al. Biochem J. Dec. 1, 2002;368(Pt 2):461-70.*
Chica et al. Curr Opin Biotechnol. Aug. 2005;16(4):378-84.*
Sen et al. Appl Biochem Biotechnol. Dec. 2007;143(3):212-23.*
Supplementary European Search Report issued Nov. 12, 2007 in the International (PCT) Application of which the present application is the U.S. National Stage.
Database UniProt, XP002454941, Database accession No. 013388, 1 p. (Jan. 1, 1998).
Database UniProt, XP002454942, Database accession No. 002490, 1 p. (Jul. 1, 1997).
Database UniProt, XP002454943, Database accession No. P49174, 1 p. (Feb. 1, 1996).
Fernández, R. C. et al., "Production of Fructooligosaccharides by β-Fructofuranosidase from Aspergillus sp 27H," XP009090866, Journal of Chemical Technology and Biotechnology, vol. 79, pp. 268-272 (2004).
Chang, C.-T. et al., "Purification and Properties of β-Fructofuranosidase from Aspergillus Oryzae ATCC 76080," XP009090867, Biochemistry and Molecular Biology International, vol. 32, No. 2, pp. 269-277 (Feb. 1994).

* cited by examiner

*Primary Examiner*—Christian L Fronda
(74) *Attorney, Agent, or Firm*—Wenderoth, Lind & Ponack, L.L.P.

(57) ABSTRACT

An object of the present invention is to provide a β-fructofuranosidase variant whose reaction specificity is improved to be suitable for the production of fructooligosaccharides. According to the present invention, there is provided a β-fructofuranosidase variant consisting of a mutated amino acid sequence of SEQ ID NO: 2 or a mutated homologue thereof, which has mutations at specific amino acid residues.

16 Claims, 2 Drawing Sheets

```
                                                       40                        60
SYHLDTTAPP  PTNLSTLPNN  TLFHVWRPRA  HILPAEGQIG  DPCAHYTDPS  TGLFHVGFLH
TYPSIDYNSA  PPNLSTLANN  SLFETWRPRA  HVLPPQNQIG  DPCMHYTDPE  TGIFHVGWLY
FHTPIDYNSA  PPNLSTLANA  SLFKTWRPRA  HLLPPSGNIG  DPCGHYTDPK  TGLFHVGWLY 62                                                                       120
DGDGIAGATT  ANLATYTDTS  DNGSFLIQPG  GKNDPVAVFD  GAVIPVGVNN  TPTLLYTSVS
NGNGASGATT  EDLVTYQDLN  PDGAQMILPG  GVNDPIAVFD  GAVIPSGIDG  KPTMMYTSVS
SG--ISGATT  DDLVTYKDLN  PDGAPSIVAG  GKNDPLSVFD  GSVIPSGIDG  MPTLLYTSVS 122    128                                       165   170          180
FLPIHWSIPY  TRGSETQSLA  VARDGGRRFD  KLDQGPVIAD  HPFAVDVTAF  RDPFVFRSAK
YMPISWALAY  TRGSETHSLA  VSSDGGKNFT  KLVQGPVIPS  PPFGANVTSW  RDPFLFQNPQ
YLPIHWSIPY  TRGSETQSLA  VSYDGGHNFT  KLNQGPVIPT  PPFALNVTAF  RDPYVFQSPI 221                     240
LDVLLSLDEE  VARNETAVQQ  AVDGWTEKNA  PWYVAVSGGV  HGVGPAQFLY  RQNGGNASEF
FDSLLE----  ----------  ------SENG  TWYTVISGGI  HGDGPSAFLY  RQHD---PDF
LDKSVN----  ----------  ------STQG  TWYVAISGGV  HGVGPCQFLY  RQND---ADF

300
QYWEYLGEWW  QEATNSSWGD  EGTWAGRWGF  NFETGNVLFL  TEEGHDPQTG  EVFVTLGTEG
QYWEYLGPWW  NEEGNSTWGS  -GDWAGRWGY  NFEVINIVGL  DDDGYNP-DG  EIFATVGTEW
QYWEYLGQWW  KEPLNTTWGK  -GDWAGGWGF  NFEVGNVFSL  NAEGYSE-DG  EIFITLGAEG 313                                                          360
SGLPIVPQVS  SIHDMLWAAG  EVGVGSEQEG  AKVEFSPSMA  GFLDWGFSAY  AAAGKVLPAS
SFDPIKPQAS  DNREMLWAAG  NMTL----ED  GDIKFTPSMA  GYLDWGLSAY  AAAGKELPAS
SGLPIVPQVS  SIRDMLWVTG  NVTN-----D  GSVTFKPTMA  GVLDWGVSAY  AAAGKILPAS
```

FIG. 1

```
                    379 381  386        395                                          420
SAVSKTSGVE  VDRYVSFVWL  TGDQYEQADG  FPTAQQGWTG  SLLLPRELKV  QTVENVVDNE
SKPS-QKSGA  PDRFVSYLWL  TGDYFEGHD-  FPTPQQNWTG  SLLLPRELSV  GTIPNVVDNE
SQAS-TKSGA  PDRFISYVWL  TGDLFEQVKG  FPTAQQNWTG  ALLLPREINV  RTISNVVDNE

480
LVREEGVSWV  VGESDNQTAR  LRTLGITIAR  ETKAALLANG  SVTAEEDRTL  QTAAVVPFAQ
LARETG-SWR  VGTNDTGVLE  LVTLKQEIAR  ETLAEMTSGN  SFT-EASRNV  SSPGSTAFQQ
LSRESLTSWR  VAREDSGQID  LETMGISISR  ETYSALTSGS  SFV-ESGKTL  SNAGAVPFNT

540
SPSSKFFVLT  AQLEFPASAR  SSPLQSGFEI  LASELERTAI  YYQFSNESLV  VDRSQTSAAA
SLDSKFFVLT  ASLSFPSSAR  DSDLKAGFEI  LSSEFESTTV  YYQFSNESII  IDRSNSSAAA
SPSSKFFVLT  ANISFPTSAR  DSGIQAGFQV  LSSSLESTTI  YYQFSNESII  VDRSNTSAAA 550                                                       600
PTNPGLDSFT  ESGKLRLFDV  IENGQEQVET  LDLTVVVDNA  VVEVYANGRF  ALSTWARSWY
LTTDGIDTRN  EFGKMRLFDV  VEGDQERIET  LDLTIVVDNS  IVEVHANGRF  ALSTWVRSWY
RTTAGILSDN  EAGRLRLFDV  LRNGKEQVET  LELTIVVDNS  VLEVYANGRF  ALGTWARSWY

DNSTQIRFFH  NGEGEVQFRN  VSVSEGLYNA  WPERN*
ESSKDIKFFH  DGDSTVQFSN  ITVYEGLFDA  WPERAR*
ANSTKINFFH  NGVGEATFED  VTVFEGLYDA  WPQRK*
```

FIG. 2

β-FRUCTOFURANOSIDASE VARIANTS

This application is a U.S. national stage of International Application No. PCT/JP2005/003787 filed Mar. 4, 2005.

FIELD OF THE INVENTION

The present invention relates to β-fructofuranosidase variants which selectively and efficiently produce specific fructooligosaccharides from sucrose, and more specifically, to β-fructofuranosidase variants which efficiently produce 1-kestose and β-fructofuranosidase variants which efficiently produce nystose.

BACKGROUND ART

Generally, fructooligosaccharides are oligosaccharides in which one to three fructose molecules are bound via β-bonds at positions C1 and C2 to the fructose moiety of sucrose and are indigestible sugars known for their excellent physiological functions, such as stimulation of the growth of bifidobacteria in the intestines, improvement in metabolism of cholesterols and other lipids, low cariogenicity, and stimulation of mineral absorption. Fructooligosaccharides are known to be widely distributed in nature in plants, such as onion, asparagus, and Jerusalem artichoke. Since technology for the mass production from sucrose utilizing a transfer reaction with β-fructofuranosidases derived from microorganisms has recently been established, they have been industrially produced. Currently, intracellular β-fructofuranosidases derived from *Aspergillus niger* are used in the industrial production of fructooligosaccharides.

Genes encoding these β-fructofuranosidases have been disclosed in WO 97/34004. However, these β-fructofuranosidases produce fructooligosaccharides as a mixture of 1-kestose, nystose, and 1-fructosylnystose and as a result the fructooligosaccharides have been manufactured and provided as syrup or powder of the oligosaccharide mixtures. If β-fructofuranosidases which selectively and efficiently produce 1-kestose or nystose as a single component can be obtained, they would provide the following advantage. Namely, by purification of 1-kestose or nystose to a high degree, followed by crystallization, it is possible to manufacture a single-component crystal fructooligosaccharide product which has excellent characteristics in terms of properties and workability while maintaining the physiological functions of the fructooligosaccharide.

On the other hand, a method for the industrial production of crystal 1-kestose using sucrose as a raw material has been disclosed, for example, in WO 97/21718. Namely, 1-kestose is produced by reacting β-fructofuranosidase with sucrose and purified to a purity of 80% or higher by chromatographic separation, after which the resulting product is used as a crystallization material to obtain crystal 1-kestose having a purity of 95% or higher. In such a method for industrial production, characteristics of enzymes for the use required are a high conversion rate from sucrose to 1-kestose and low nystose production. Similarly, in a method for the industrial production of nystose as a single component, characteristics of the enzymes required are a high conversion rate to nystose and low 1-fructosylnystose production.

SUMMARY OF THE INVENTION

An object of the present invention is to provide β-fructofuranosidase variants whose reaction specificities are improved to be suitable for the production of single components of fructooligosaccharides, such as 1-kestose and nystose, and genes of the variants.

The present inventors have found that β-fructofuranosidase variants in which amino acid residues at specific positions in the amino acid sequence of SEQ ID NO: 2 are substituted with other amino acid residues have reaction specificities suitable for the production of 1-kestose or nystose.

Namely, according to the first embodiment of the present invention, there is provided a β-fructofuranosidase variant consisting of (a) a mutated amino acid sequence of SEQ ID NO: 2, which has at least one mutation in amino acid residues at positions 62, 122, 128, 165, 221, 395, and 550 or (b) a mutated homologue of the amino acid sequence of SEQ ID NO: 2, which has at least one mutation in amino acid residues corresponding to the amino acid residues at positions 62, 122, 128, 165, 221, 395, and 550 of SEQ ID NO: 2.

According to the second embodiment of the present invention, there is provided a β-fructofuranosidase variant consisting of (c) a mutated amino acid sequence of SEQ ID NO: 2, which has at least one mutation in amino acid residues at positions 40, 379, and 381 or (d) a mutated homologue of the amino acid sequence of SEQ ID NO: 2, which has at least one mutation in amino acid residues corresponding to the amino acid residues at positions 40, 379, and 381 of SEQ ID NO: 2.

With the use of β-fructofuranosidase variants according to the present invention, it is possible to improve the sugar composition of an enzyme reaction solution upon producing fructooligosaccharides and efficiently produce single component fructooligosaccharides. Namely, β-fructofuranosidase variants according to the present invention advantageously enable the industrial production of a single component fructooligosaccharide more easily and less costly than conventional methods.

BRIEF DESCRIPTION OF THE DRAWINGS

FIG. 1 illustrates an example of the alignment of the amino acid sequence represented by SEQ ID NO: 2 and its homologues. The top line shows the amino acid sequence (SEQ ID NO: 2) of β-fructofuranosidase derived from *A. niger*, the middle line shows the amino acid sequence (SEQ ID NO: 6) of β-fructofuranosidase derived from *S. brevicaulis*, and the bottom line shows the amino acid sequence (SEQ ID NO: 4) of β-fructofuranosidase derived from *P. roqueforiti*. The numbers in the Figure are amino acid numbers setting the N terminal amino acid of the *A. niger*-derived sequence to be 1. Specific mutation sites are shown with frames.

FIG. 2 illustrates a continuation of the amino acid sequences in FIG. 1.

DETAILED DESCRIPTION OF THE INVENTION

β-Fructofuranosidase Variants and their Genes

The variants according to the first and the second embodiments of the present invention consist of mutated amino acid sequences or mutated homologues of SEQ ID NO: 2, in which a mutation is introduced into at least one specific amino acid residue.

Position numbers of the amino acid residues into which mutations are introduced correspond to the numbers of the amino acid residues of the amino acid sequence represented by SEQ ID NO: 2.

In the present invention, the term "mutation" refers to a substitution, deletion or insertion.

The term "substitution" means that a specific amino acid residue at a specific position is removed and another amino acid residue is inserted into the same position.

The term "deletion" means that a specific amino acid residue is removed.

The term "insertion" means that one or more amino acid residues are inserted before or after a specific amino acid residue, more specifically, that one or more, preferably one or several, amino acid residues are bound to an α-carboxyl group or an α-amino group of the specific amino acid residue.

The number of the specific mutations introduced into the amino acid sequence of SEQ ID NO: 2 and its homologues is not particularly limited and can be one or several, one to three, or one or two.

In the variants according to the first and the second embodiments of the present invention, the mutations introduced into the amino acid sequence of SEQ ID NO: 2 and its homologues are preferably substitutions.

In the variants according to the first embodiment of the present invention, substitutions introduced into the amino acid residues at positions 62, 122, 128, 165, 221, 395, and 550 of the amino acid sequence of SEQ ID NO: 2 and its homologues are preferably as follows:

a substitution of the amino acid residue at position 62 with an acidic amino acid selected from the group consisting of aspartic acid and glutamic acid, in particular, with glutamic acid;

a substitution of the amino acid residue at position 122 with an amino acid selected from the group consisting of methionine, isoleucine, leucine, and valine, in particular, with methionine;

a substitution of the amino acid residue at position 128 with an amino acid selected from the group consisting of asparagine and glutamine, in particular, with asparagine;

a substitution of the amino acid residue at position 165 with an aromatic amino acid selected from the group consisting of tryptophan, phenylalanine, and tyrosine, in particular, with phenylalanine;

a substitution of the amino acid residue at position 221 with an aromatic amino acid selected from the group consisting of tryptophan, phenylalanine, and tyrosine, in particular, with tyrosine;

a substitution of the amino acid residue at position 395 with an amino acid selected from the group consisting of leucine, methionine, isoleucine, and valine, in particular, with leucine; and a substitution of the amino acid residue at position 550 with a hydroxy amino acid selected from the group consisting of serine and threonine, in particular, with serine.

The variants according to the first embodiment of the present invention may further have mutations, preferably substitutions, in at least one amino acid residue at positions 170, 300, 313, and 386 of the amino acid sequence of SEQ ID NO: 2 and its homologues. Advantageously, β-fructofuranosidases having these mutations can selectively and efficiently produce 1-kestose (for example, see WO 99/13059).

In the variants according to the first embodiment of the present invention, substitutions which can be introduced into the amino acid residues at positions 170, 300, 313, and 386 of the amino acid sequence of SEQ ID NO: 2 and its homologues are preferably as follows:

a substitution of the amino acid residue at position 170 with an aromatic amino acid selected from the group consisting of tryptophan, phenylalanine, and tyrosine, in particular, with tryptophan;

a substitution of the amino acid residue at position 300 with an amino acid selected from the group consisting of tryptophan, phenylalanine, tyrosine, and valine, in particular, with valine;

a substitution of the amino acid residue at position 313 with a basic amino acid selected from the group consisting of lysine, arginine, and histidine, in particular, with lysine or arginine; and a substitution of the amino acid residue at position 386 with a basic amino acid selected from the group consisting of lysine, arginine, and histidine, in particular, with lysine.

In the variants according to the first embodiment of the present invention, an example of preferred multiple mutations which can be introduced into the amino acid sequence of SEQ ID NO: 2 and its homologues is a triple mutation, preferably a triple substitution, in the amino acid residue at position 165, the amino acid residue at position 300, and the amino acid residue at position 313; in particular, a triple substitution consisting of a substitution of the amino acid residue at position 165 with an aromatic amino acid selected from the group consisting of tryptophan, phenylalanine, and tyrosine (most preferably a substitution with phenylalanine), a substitution of the amino acid residue at position 300 with an amino acid selected from the group consisting of tryptophan, phenylalanine, tyrosine and valine (most preferably a substitution with valine), and a substitution of the amino acid residue at position 313 with a basic amino acid selected from the group consisting of lysine, arginine, and histidine (most preferably a substitution with lysine or arginine).

In the variants according to the second embodiment of the present invention, substitutions which are introduced into the amino acid residues at positions 40, 379, and 381 of the amino acid sequence of SEQ ID NO: 2 and its homologues are preferably as follows:

a substitution of the amino acid residue at position 40 with an acidic amino acid selected from the group consisting of aspartic acid and glutamic acid, in particular, with aspartic acid;

a substitution of the amino acid residue at position 379 with cysteine; and a substitution of the amino acid residue at position 381 with an amino acid selected from the group consisting of methionine, isoleucine, leucine, and valine, in particular, with methionine.

In the variants according to the first and the second embodiments of the present invention, the term "homologue" refers to a variant of the amino acid sequence of SEQ ID NO: 2, which has one or more mutations and has β-fructofuranosidase activity. The number of mutations can be 1 to several or 1, 2, 3, or 4.

In the present invention, whether a homologue has β-fructofuranosidase activity or not can be evaluated, for example, by reacting the protein consisting of the amino acid sequence of interest with a substrate and detecting the reaction product. For example, it can be evaluated according to the method described in Example 2.

The positions of specific mutations according to the present invention in a homologue are determined based on the position numbers of the amino acid residues in SEQ ID NO: 2 corresponding to the homologue by aligning the amino acid sequence of SEQ ID NO: 2 with said homologue. For example, "a mutation of the amino acid residue at position 62" in a homologue does not mean a mutation of the amino acid residue at position 62 of the homologue but a mutation of an amino acid residue of the homologue which corresponds to the amino acid residue at position 62 of the amino acid sequence of SEQ ID NO: 2. An example of the alignment of the amino acid sequence of SEQ ID NO: 2 and its homologues is shown in FIG. 1 and FIG. 2.

The alignment of the amino acid sequence of SEQ ID NO: 2 and its homologues can be carried out using an analytical software tool to examine the sequence homology. Such software tool is widely known and naturally can be appropriately selected for use by those skilled in the art. For example, by using the BLAST method (Basic Local Alignment Search Tool; Altschul, S. F. et al., J. Mol. Biol., 215, 403-410 (1990)), the amino acid sequence of SEQ ID NO: 2 and its homologue can be aligned to determine corresponding amino acid residues.

An example of the homologues is a variant of the amino acid sequence of SEQ ID NO: 2, which has one or more (for example, one to several, or 1, 2, 3, or 4) mutations having no effect on β-fructofuranosidase activity.

Examples of "mutations having no effect on activity" include conservative substitutions. The term "conservative substitutions" means that one or more amino acid residues are substituted with other chemically homologous amino acid residues so as not to substantially change protein activity. Examples of such substitutions include the substitution of a certain hydrophobic residue with another hydrophobic residue and the substitution of a certain polar residue with another polar residue having the same electric charge. Functionally homologous amino acids of different types which can be substituted in such a manner are known to those skilled in the art. Specific examples of such amino acids include non-polar (hydrophobic) amino acids, such as alanine, valine, isoleucine, leucine, proline, tryptophan, phenylalanine, and methionine; polar (neutral) amino acids, such as glycine, serine, threonine, tyrosine, glutamine, asparagine, and cysteine; positively charged (basic) amino acids, such as arginine, histidine, and lysine; and further, negatively charged (acidic) amino acids, such as aspartic acid and glutamic acid.

Examples of the "homologues" include β-fructofuranosidases produced by microorganisms which belong to the genus *Aspergillus*, the genus *Penicillium*, and the genus *Scopulariopsis*, such as β-fructofuranosidase from *Aspergillus niger*, β-fructofuranosidase from *Penicillium roqueforiti*, and β-fructofuranosidase from *Scopulariopsis brevicaulis*. An example of the β-fructofuranosidase from *Penicillium roqueforiti* is the protein (SEQ ID NO: 4) consisting of the amino acid sequence of SEQ ID NO: 1 in WO 99/13059. An example of the β-fructofuranosidase from *Scopulariopsis brevicaulis* is the protein (SEQ ID NO: 6) consisting of the amino acid sequence of SEQ ID NO: 3 in WO 99/13059.

According to the present invention, there are provided genes encoding the β-fructofuranosidase variants according to the present invention.

Generally, once the amino acid sequence of a protein is provided, a DNA sequence which encodes the protein can be easily determined from the codon table. Accordingly, it is possible to appropriately select a variety of DNA sequences which encode the amino acid sequence of SEQ ID NO: 1 and its homologue into which specific mutations according to the present invention are introduced, such as the amino acid sequences of SEQ ID NO: 2, SEQ ID NO: 4, and SEQ ID NO: 6 into which specific mutations according to the present invention are introduced. Therefore, the DNA sequence encoding a β-fructofuranosidase variant into which specific mutations according to the present invention are introduced refers not only to a β-fructofuranosidase gene which has DNA mutations corresponding to specific amino acid mutations according to the present invention but also to a DNA sequence which has the same DNA sequence, except that degenerate codons are used, and encodes the β-fructofura-nosidase variant. For example, the DNA sequences encoding amino acid sequences of SEQ ID NO: 2, 4, and 6, into which specific mutations according to the present invention are introduced, refer not only to the DNA sequences of SEQ ID NO: 1, 3, and 5 which have one or more mutations shown in Table 3 (described later) but also to DNA sequences which have the same DNA sequences, except that degenerate codons are used, and encode β-fructofuranosidase variants.

Preparation of β-Fructofuranosidase Variants

A β-Fructofuranosidase variant can be prepared using recombinant DNA technology, polypeptide synthesis technology, and the like. With the use of recombinant DNA technology, DNA encoding β-fructofuranosidase (for example, the DNA sequence of SEQ ID NO: 1, 3, or 5) is obtained and site-specific mutations or random mutations are generated in this DNA to substitute amino acids to be encoded, after which a host cell is transformed with an expression vector containing the DNA treated for mutations and the resulting transformants are cultured to prepare a β-fructofuranosidase variant.

The method for the introduction of site-specific mutations into the gene can be a method known to those skilled in the art, such as the gapped duplex method and the Kunkel method. These methods can be utilized to generate mutations at specific sites of DNA encoding β-fructofuranosidase.

For the introduction of random mutations, a generally used method such as the error-prone PCR method can be used. The DNA base sequence after the mutation treatment can be confirmed by the Maxam-Gilbert chemical modification method or the dideoxynucleotide chain termination method. The amino acid sequence of the β-fructofuranosidase variant can be decoded from the confirmed nucleotide sequence.

Production of β-Fructofuranosidase Variants

A β-fructofuranosidase variant can be prepared by preparing a recombinant vector in which a DNA fragment encoding it is linked to a DNA molecule, in particular a DNA expression vector, which is replicable in a host cell and contains its gene in expressible conditions, introducing this recombinant vector into a host for transformation, and culturing the resulting transformants under appropriate culture conditions.

The vector used in the present invention can be appropriately selected from viruses, plasmids, cosmid vectors and the like taking the kind of host cell to be used into consideration. Examples of the vectors include pUC and pBR plasmids for *Escherichia coli*, pUB plasmids for *Bacillus subtilis*, and YEp, YRp, YCp plasmid vectors for yeasts.

According to a preferred embodiment of the present invention, a plasmid can be used as a recombinant vector. The plasmid preferably contains a selectable marker for transformation and a drug-resistance marker or a gene complementing a host auxotrophy can be used as a selectable maker. Preferred specific examples of the selectable marker include the ampicillin-resistance gene, the kanamycin-resistance gene, and the tetracycline-resistance gene for bacterial host cells; the tryptophan biosynthesis gene (TRP1), the uracyl biosynthesis gene (URA3), and the leucine biosynthesis gene (LEU2) for yeasts; and the hygromycin-resistance gene (Hyg), the bialaphos-resistance gene (Bar), and the nitrate reductase gene (niaD) for fungi.

The DNA molecule for use as an expression vector according to the present invention preferably contains nucleotide sequences necessary for the expression of a mutant gene, including transcription and translation control signals, such as a promoter, a transcription initiation signal, a ribosome binding site, a translation termination signal, and a transcription termination signal.

Preferred examples of the promoter include, not to mention a promoter which is contained in an inserted fragment and can function in the host, the promoters of the lactose operon (lac) and the tryptophan operon (trp) for *E. coli*; the promoters of the alcohol dehydrogenase (ADH) gene, the acid phosphatase (PHO) gene, the galactose (GAL) gene, and the glyceraldehyde-3-phosphate dehydrogenase (GPD) gene for yeasts; and the promoters of the α-amylase (amy) gene and the cellobiohydrolase I (CBHI) gene for fungi.

As a host, any cell with an established host-vector system, preferably for example, a yeast or a fungus, can be used. A transformant obtained by the transformation of the host cell is cultured under appropriate conditions and the resulting culture is subjected to a general procedure for enzyme fractionation and purification to obtain a β-fructofuranosidase variant. Further, when the host cell is *Bacillus subtilis*, a yeast or a fungus, a secretion vector is advantageously used to extracellularly secrete the recombinant β-fructofuranosidase.

The variant according to the present invention produced using the transformant can be obtained as follows. First, the abovementioned host cell is cultured under appropriate conditions and the culture supernatant or cells are obtained from the resultant culture using a known method such as centrifugation. The cells are further suspended in an appropriate buffer solution and then destructed by means of freezing and thawing, ultrasonication or crushing and the resulting product is centrifuged or filtered to obtain a cell extract containing the recombinant enzyme.

The enzyme can be purified by an appropriate combination of commonly used processes for separation and purification. Examples of such processes include those which utilize the difference in thermal resistance, such as heat treatment; those which utilize the difference in solubility, such as salt precipitation and solvent precipitation; those which utilize the difference in molecular weight, such as dialysis, ultrafiltration, gel filtration, and SDS-polyacrylamide gel electrophoresis; those which utilize the difference in electric charge, such as ion exchange chromatography; those which utilize specific affinity, such as affinity chromatography; those which utilize the difference in hydrophobicity, such as hydrophobic chromatography and reversed-phase chromatography; and those which utilize the difference in isoelectric point, such as isoelectric electrophoresis.

Production of Fructooligosaccharides

According to the present invention, there is provided a method for the production of fructooligosaccharides using a transformant according to the present invention or a β-fructofuranosidase variant according to the present invention. Specifically, the method for the production of fructooligosaccharides according to the present invention is carried out by bringing the transformant according to the present invention or the β-fructofuranosidase variant according to the present invention into contact with sucrose.

The mode and conditions for bringing the transformant according to the present invention or the β-fructofuranosidase variant according to the present invention into contact with sucrose are not particularly limited as long as the variant is able to act on sucrose. A preferred embodiment in which the contact proceeds in solution is as follows. Namely, the sucrose concentration can be appropriately selected within the range where the sugar to be used is soluble, taking the specific activity and reaction temperature of the enzyme into consideration. It ranges generally from 5 to 80%, preferably from 30 to 70%. The temperature and pH conditions for the reaction of the sugar and the enzyme are preferably optimized for the variant and generally range from about 30 to 80° C. and from pH 4 to 10, preferably from 40 to 70° C. and from pH 5 to 7.

Further, the degree of purification of the variant can be appropriately selected. The variant to be used can be a crude enzyme from culture supernatant or crushed cells of the transformant or a purified enzyme obtained by various purification processes. Alternatively, it can be used as an isolated purified enzyme obtained by additional various purification processes.

Furthermore, the enzyme can be brought into contact with sucrose in an immobilized form onto a carrier according to an ordinary method.

Fructooligosaccharides can be purified from the resulting reaction solution according to a known method. For example, the solution is heated to inactivate the enzyme, decolorized using activated carbon, and then desalted using ion exchange resins.

When the variant of the first embodiment of the present invention is used for the preparation of fructooligosaccharides, the production of 1-kestose is increased and the production of nystose is decreased. Therefore, according to the present invention, there is provided a method for the selective production of 1-kestose. Namely, according to the present invention, there is provided a method for the production of 1-kestose, comprising the step of bringing the β-fructofuranosidase variant of the first embodiment or a transformant which can express a polynucleotide encoding the β-fructofuranosidase variant of the first embodiment into contact with sucrose.

When the variant of the second embodiment of the present invention is used for the preparation of fructooligosaccharides, the production of nystose is increased and the production of 1-kestose is decreased. Therefore, according to the present invention, there is provided a method for the selective production of nystose. Namely, according to the present invention, there is provided a method for the production of nystose, comprising the step of bringing the β-fructofuranosidase variant of the second embodiment or a transformant which can express a polynucleotide encoding the β-fructofuranosidase variant of the second embodiment into contact with sucrose.

EXAMPLES

The present invention will be illustrated more in detail with reference to the following examples; however, these examples are not construed to limit the scope of the invention.

Example 1

Preparation of β-Fructofuranosidase Variants

Introduction of random mutations into the β-fructofuranosidase gene was carried out using a commercially available PCR mutagenesis kit (Gene Morph, Stratagene) as follows. The β-fructofuranosidase gene from the ATCC 20611 strain (*A. niger*) was used as a template DNA. Specifically, plasmid pAW20-Hyg described in WO 97/34004 was used. A PCR reaction solution contained 1 μl of template DNA, 1 μl of 40 mM dNTP, 5 μl of a 10-fold concentrated buffer solution, 0.5 μl each of 250 ng/ml 5'-GCGAATTCATGAAGCTCAC-CACTACCA-3' (N-terminal) (SEQ ID NO: 7) and 5'-GCG-GATCCCGGTCAATTTCTCT-3' (C-terminal) (SEQ ID NO: 8) as primers, 1 μl of Mutazyme, 5 μl of DMSO, and 36 μl of sterile water to make the total volume 50 μl. The reaction was carried out by 30 cycles of incubation at 94° C. for 1 minute (denaturation step), at 50° C. for 2 minutes (annealing step), and at 72° C. for 2.5 minutes (elongation step), after pretreatment at 94° C. for 2 minutes. Finally, incubation was carried out at 72° C. for 3 minutes to complete the reaction. The reaction solution was subjected to extraction with phenol/chloroform/isoamyl alcohol and then precipitation with ethanol. The precipitate was dissolved in a TE buffer solution, after which the resulting solution was subjected to agarose gel electrophoresis and a specifically amplified band of 1.9 kbp was excised to recover a DNA fragment according to an ordinary method. A plasmid in which the 1.9 kbp EcoRI-BamHI fragment was inserted into the EcoRI-BamHI site of pY2831 was introduced into the *S. cerevisiae* MS-161 strain by the lithium acetate method to obtain a transformant, according to the method described in WO 97/34004. The transformant thus obtained was cultured in an SD-GF medium (0.67% yeast nitrogen base without amino acids, 2% sucrose, 2% casamino acids, and 50 μg/ml uracyl) at 30° C. for 3 days to obtain a β-fructofuranosidase variant.

Example 2

Evaluation of Reaction Specificity of β-Fructofuranosidase Variants

The enzyme reaction was carried out at pH 7 at 40° C. using the β-fructofuranosidase variants prepared in Example 1 and sucrose as a substrate at a substrate concentration of 48% and the sugar composition of each resulting reaction solution was subjected to HPLC analysis. The sugar composition of each enzyme reaction solution was compared with the sugar composition with the wild-type β-fructofuranosidase and variants showing altered compositions were selected as β-fructofuranosidase variants with altered reaction specificity.

In order to identify mutation points of the β-fructofuranosidase variants with altered reaction specificity, DNA base sequences were analyzed. Sequencing reaction was carried out using a DNA sequencing kit by Pharmacia. Samples after the reaction were analyzed using DNA sequencer (ALFred) by Pharmacia to obtain base sequences of individual DNA fragments. Then, final base sequences were obtained using a DNA analysis software (DNASIS, Hitachi Software Engineering) to determine the mutation points into which random mutations were introduced. As a result, as shown in Table 1 and Table 2, it was revealed that β-fructofuranosidase variants which efficiently produce 1-kestose and β-fructofuranosidase variants which efficiently produce nystose were obtained.

TABLE 1

β-fructofuranosidase variants with which 1-kestose production is increased and nystose production is decreased

|  | F | G | GF | $GF_2$ | $GF_3$ | $GF_4$ |
|---|---|---|---|---|---|---|
| Wild-type | 0.4 | 22.3 | 20.5 | 45.1 | 11.3 | 0.3 |
| G62E | 0.6 | 22.1 | 21.1 | 46.0 | 10.0 | 0.2 |
| L122M | 0.7 | 22.1 | 19.7 | 47.9 | 9.6 | 0.0 |
| I128N | 0.8 | 20.7 | 26.5 | 45.1 | 6.5 | 0.5 |
| V165F | 0.6 | 22.0 | 19.8 | 46.8 | 10.8 | 0.0 |
| H221Y | 0.6 | 23.8 | 20.1 | 45.8 | 9.5 | 0.2 |
| Q395L | 0.6 | 22.1 | 21.4 | 46.5 | 9.1 | 0.2 |
| T550S | 0.9 | 26.3 | 13.1 | 48.4 | 10.4 | 0.9 |

F: Fructose
G: Glucose
GF: Sucrose
$GF_2$: 1-Kestose
$GF_3$: Nystose
$GF_4$: 1-Fructosylnystose

TABLE 2

β-fructofuranosidase variants with which nystose production is increased and 1-kestose production is decreased

|  | F | G | GF | $GF_2$ | $GF_3$ | $GF_4$ |
|---|---|---|---|---|---|---|
| Wild-type | 0.4 | 22.3 | 20.5 | 45.1 | 11.3 | 0.3 |
| G40D | 0.6 | 22.3 | 20.3 | 41.6 | 14.7 | 0.5 |
| T381M | 1.5 | 23.7 | 23.9 | 28.8 | 19.3 | 2.8 |
| W379C | 1.1 | 22.6 | 22.5 | 36.2 | 17.0 | 0.6 |

F: Fructose
G: Glucose
GF: Sucrose
$GF_2$: 1-Kestose
$GF_3$: Nystose
$GF_4$: 1-Fructosylnystose Mutations obtained and their corresponding DNA sequences are as follows. Underlined are mutated DNAs.

TABLE 3

Amino acid residues and DNA sequences at mutation sites

| G62E | GAC G<u>A</u>G GAC | (SEQ ID NO: 9) |
|  | Asp Glu Asp |  |
| L122M | TTC <u>A</u>TG CCC | (SEQ ID NO: 10) |
|  | Phe Met Pro |  |
| I128N | TCC A<u>A</u>C CCC | (SEQ ID NO: 11) |
|  | Ser Asn Pro |  |
| V165F | GCC <u>TT</u>C GAC | (SEQ ID NO: 12) |
|  | Ala Phe Asp |  |
| H221Y | GTG T<u>A</u>C GGC | (SEQ ID NO: 13) |
|  | Val Tyr Gly |  |
| Q395L | GCC C<u>T</u>G CAG | (SEQ ID NO: 14) |
|  | Ala Leu Gln |  |
| T550S | TTT <u>TC</u>G GAG | (SEQ ID NO: 15) |
|  | Phe Ser Glu |  |
| G40D | ATC G<u>A</u>C GAC | (SEQ ID NO: 16) |
|  | Ile Asp Asp |  |
| T381M | TTG A<u>T</u>G GGC | (SEQ ID NO: 17) |
|  | Leu Met Gly |  |
| W379C | GTC TG<u>C</u> TTG | (SEQ ID NO: 18) |
|  | Val Cys Leu |  |

Example 3

Preparation of Multiple Substitution Variants by Site-directed Mutations and Evaluation of their Reaction Specificity A ternary substitution variant was prepared by introducing site-directed mutations using the combination of V165F obtained in Example 2 and G300V and H313K described in WO 97/34004. Specifically, the β-fructofuranosidase gene prepared in Examples 1 and 2, into which the mutation V165F was introduced, was inserted into the EcoRI-BamHI site of pUC118 (Takara Shuzo) to prepare a plasmid. Next, the mutations G300V and H313K were introduced one by one in the same manner as described in Example D8 in WO 97/34004. The DNA base sequences were examined in the same manner as in Example 2, which confirmed that the base sequences at the site of interest only were substituted.

The reaction specificity of the ternary substitution variant V165F+G300V+H313K was examined according to the method in Example 2. The result is shown in Table 4. The 1-kestose production was increased about 10% and the nystose production was decreased 7% with the ternary substitution variant as compared to those with the wild-type β-fructofuranosidase.

TABLE 4

| Reaction specificity of ternary substitution variant | | | | | | |
|---|---|---|---|---|---|---|
| | F | G | GF | $GF_2$ | $GF_3$ | $GF_4$ |
| Wild-type | 0.4 | 22.3 | 20.5 | 45.1 | 11.3 | 0.3 |
| V165F/G300V/H313K | 1.7 | 22.5 | 15.8 | 55.7 | 4.3 | 0.0 |

F: Fructose
G: Glucose
GF: Sucrose
$GF_2$: 1-Kestose
$GF_3$: Nystose
$GF_4$: 1-Fructosylnystose

The invention claimed is:

1. An isolated β-fructofuranosidase variant consisting of the following amino acid sequence:
   (a) a mutated amino acid sequence of SEQ ID NO: 2, which has at least one mutation in amino acid residues at positions 62, 122, 128, 165, 221, 395, and 550, or
   (b) a mutated amino acid sequence of SEQ ID NO: 4 or SEQ ID NO: 6, which has at least one mutation in amino acid residues corresponding to the amino acid residues at positions 62, 122, 128, 165, 221, 395, and 550 of SEQ ID NO: 2.

2. The variant according to claim 1, wherein the mutation is a substitution.

3. The variant according to claim 2, wherein the substitution is
   a substitution of the amino acid residue at position 62 with an acidic amino acid selected from the group consisting of aspartic acid and glutamic acid;
   a substitution of the amino acid residue at position 122 with an amino acid selected from the group consisting of methionine, isoleucine, leucine, and valine;
   a substitution of the amino acid residue at position 128 with an amino acid selected from the group consisting of asparagine and glutamine;
   a substitution of the amino acid residue at position 165 with an aromatic amino acid selected from the group consisting of tryptophan, phenylalanine, and tyrosine;
   a substitution of the amino acid residue at position 221 with an aromatic amino acid selected from the group consisting of tryptophan, phenylalanine, and tyrosine;
   a substitution of the amino acid residue at position 395 with an amino acid selected from the group consisting of leucine, methionine, isoleucine, and valine; or
   a substitution of the amino acid residue at position 550 with a hydroxy amino acid selected from the group consisting of serine and threonine.

4. The variant according to claim 1, 2, or 3, which further has a mutation in at least one amino acid residue at positions 170, 300, 313, and 386 of the C amino acid sequence represented by SEQ ID NO: 2.

5. The variant according to claim 4, wherein the mutation is a substitution.

6. The variant according to claim 5, wherein the substitution is
- a substitution of the amino acid residue at position 170 with an aromatic amino acid selected from the group consisting of tryptophan, phenylalanine, and tyrosine;
- a substitution of the amino acid residue at position 300 with an amino acid selected from the group consisting of tryptophan, phenylalanine, tyrosine, and valine;
- a substitution of the amino acid residue at position 313 with a basic amino acid selected from the group consisting of lysine, arginine, and histidine; or
- a substitution of the amino acid residue at position 386 with a basic amino acid selected from the group consisting of lysine, arginine, and histidine.

7. The variant according to claim 4, which has mutations in the amino acid residues at positions 165, 300 and 313.

8. The variant according to claim 7, wherein the mutations are substitutions.

9. The variant according to claim 8, wherein the substitutions are
- a substitution of the amino acid residue at position 165 with an aromatic amino acid selected from the group consisting of tryptophan, phenylalanine, and tyrosine;
- a substitution of the amino acid residue at position 300 with an amino acid selected from the group consisting of tryptophan, phenylalanine, tyrosine and valine; and
- a substitution of the amino acid residue at position 313 with a basic amino acid selected from the group consisting of lysine, arginine, and histidine.

10. An isolated β-fructofuranosidase variant consisting of the following amino acid sequence:
- (c) a mutated amino acid sequence of SEQ ID NO: 2, which has at least one mutation in amino acid residues at positions 40, 379, and 381, or
- (d) a mutated amino acid sequence of SEQ ID NO: 4 or SEQ ID NO: 6, which has at least one mutation in amino acid residues corresponding to the amino acid residues at positions 40, 379, and 381 of SEQ ID NO: 2.

11. The variant according to claim 10, wherein the mutation is a substitution.

12. The variant according to claim 11, wherein the substitution is
- a substitution of the amino acid residue at position 40 with an acidic amino acid selected from the group consisting of aspartic acid and glutamic acid;
- a substitution of the amino acid residue at position 379 with cysteine; or
- a substitution of the amino acid residue at position 381 with an amino acid selected from the group consisting of methionine, isoleucine, leucine, and valine.

13. An isolated polynucleotide encoding the β-fructofuranosidase variant of claim 1 or 10.

14. A recombinant vector comprising the polynucleotide of claim 13.

15. A transformant comprising the recombinant vector of claim 14.

16. A method for producing a fructooligosaccharide, which comprises the step of bringing the transformant of claim 15 or the β-fructofuranosidase variant of claim 1 or 10 into contact with sucrose.

* * * * *

SEQUENCE LISTING

<160> NUMBER OF SEQ ID NOS: 18

<210> SEQ ID NO 1
<211> LENGTH: 1905
<212> TYPE: DNA
<213> ORGANISM: Aspergillus niger
<220> FEATURE:
<221> NAME/KEY: CDS
<222> LOCATION: (1)..(1905)

<400> SEQUENCE: 1

```
tca tac cac ctg gac acc acg gcc ccg ccg acc aac ctc agc acc        48
Ser Tyr His Leu Asp Thr Thr Ala Pro Pro Thr Asn Leu Ser Thr
1               5                   10                  15 ctc ccc aac aac acc ctc ttc cac gtg tgg cgg ccg cgc gcg cac atc    96
Leu Pro Asn Asn Thr Leu Phe His Val Trp Arg Pro Arg Ala His Ile
                20                  25                  30 ctg ccc gcc gag ggc cag atc ggc gac ccc tgc gcg cac tac acc gac   144
Leu Pro Ala Glu Gly Gln Ile Gly Asp Pro Cys Ala His Tyr Thr Asp
            35                  40                  45 cca tcc acc ggc ctc ttc cac gtg ggg ttc ctg cac gac ggg gac ggc   192
Pro Ser Thr Gly Leu Phe His Val Gly Phe Leu His Asp Gly Asp Gly
        50                  55                  60 atc gcg ggc gcc acc acg gcc aac ctg gcc acc tac acc gat acc tcc   240
Ile Ala Gly Ala Thr Thr Ala Asn Leu Ala Thr Tyr Thr Asp Thr Ser
65                  70                  75                  80 gat aac ggg agc ttc ctg atc cag ccg ggc ggg aag aac gac ccc gtc   288
Asp Asn Gly Ser Phe Leu Ile Gln Pro Gly Gly Lys Asn Asp Pro Val
                85                  90                  95 gcc gtg ttc gac ggc gcc gtc atc ccc gtc ggc gtc aac aac acc ccc   336
Ala Val Phe Asp Gly Ala Val Ile Pro Val Gly Val Asn Asn Thr Pro
                100                 105                 110 acc tta ctc tac acc tcc gtc tcc ttc ctg ccc atc cac tgg tcc atc   384
Thr Leu Leu Tyr Thr Ser Val Ser Phe Leu Pro Ile His Trp Ser Ile
            115                 120                 125 ccc tac acc cgc ggc agc gag acg cag tcg ttg gcc gtc gcg cgc gac   432
Pro Tyr Thr Arg Gly Ser Glu Thr Gln Ser Leu Ala Val Ala Arg Asp
        130                 135                 140 ggc ggc cgc cgc ttc gac aag ctc gac cag ggc ccc gtc atc gcc gac   480
Gly Gly Arg Arg Phe Asp Lys Leu Asp Gln Gly Pro Val Ile Ala Asp
145                 150                 155                 160 cac ccc ttc gcc gtc gac gtc acc gcc ttc cgc gat ccg ttt gtc ttc   528
His Pro Phe Ala Val Asp Val Thr Ala Phe Arg Asp Pro Phe Val Phe
```

-continued

```
                      165                 170                 175
cgc agt gcc aag ttg gat gtg ctg ctg tcg ttg gat gag gag gtg gcg      576
Arg Ser Ala Lys Leu Asp Val Leu Leu Ser Leu Asp Glu Glu Val Ala
            180                 185                 190 cgg aat gag acg gcc gtg cag cag gcc gtc gat ggc tgg acc gag aag      624
Arg Asn Glu Thr Ala Val Gln Gln Ala Val Asp Gly Trp Thr Glu Lys
        195                 200                 205 aac gcc ccc tgg tat gtc gcg gtc tct ggc ggg gtg cac ggc gtc ggg      672
Asn Ala Pro Trp Tyr Val Ala Val Ser Gly Gly Val His Gly Val Gly
    210                 215                 220 ccc gcg cag ttc ctc tac cgc cag aac ggc ggg aac gct tcc gag ttc      720
Pro Ala Gln Phe Leu Tyr Arg Gln Asn Gly Gly Asn Ala Ser Glu Phe
225                 230                 235                 240 cag tac tgg gag tac ctc ggg gag tgg tgg cag gag gcg acc aac tcc      768
Gln Tyr Trp Glu Tyr Leu Gly Glu Trp Trp Gln Glu Ala Thr Asn Ser
                245                 250                 255 agc tgg ggc gac gag ggc acc tgg gcc ggg cgc tgg ggg ttc aac ttc      816
Ser Trp Gly Asp Glu Gly Thr Trp Ala Gly Arg Trp Gly Phe Asn Phe
            260                 265                 270 gag acg ggg aat gtg ctc ttc ctc acc gag gag ggc cat gac ccc cag      864
Glu Thr Gly Asn Val Leu Phe Leu Thr Glu Glu Gly His Asp Pro Gln
        275                 280                 285 acg ggc gag gtg ttc gtc acc ctc ggc acg gag ggg tct ggc ctg cca      912
Thr Gly Glu Val Phe Val Thr Leu Gly Thr Glu Gly Ser Gly Leu Pro
    290                 295                 300 atc gtg ccg cag gtc tcc agt atc cac gat atg ctg tgg gcg gcg ggt      960
Ile Val Pro Gln Val Ser Ser Ile His Asp Met Leu Trp Ala Ala Gly
305                 310                 315                 320 gag gtc ggg gtg ggc agt gag cag gag ggt gcc aag gtc gag ttc tcc     1008
Glu Val Gly Val Gly Ser Glu Gln Glu Gly Ala Lys Val Glu Phe Ser
                325                 330                 335 ccc tcc atg gcc ggg ttt ctg gac tgg ggg ttc agc gcc tac gct gcg     1056
Pro Ser Met Ala Gly Phe Leu Asp Trp Gly Phe Ser Ala Tyr Ala Ala
            340                 345                 350 gcg ggc aag gtg ctg ccg gcc agc tcg gcg gtg tcg aag acc agc ggc     1104
Ala Gly Lys Val Leu Pro Ala Ser Ser Ala Val Ser Lys Thr Ser Gly
        355                 360                 365 gtg gag gtg gat cgg tat gtc tcg ttc gtc tgg ttg acg ggc gac cag     1152
Val Glu Val Asp Arg Tyr Val Ser Phe Val Trp Leu Thr Gly Asp Gln
    370                 375                 380 tac gag cag gcg gac ggg ttc ccc acg gcc cag cag ggg tgg acg ggg     1200
Tyr Glu Gln Ala Asp Gly Phe Pro Thr Ala Gln Gln Gly Trp Thr Gly
385                 390                 395                 400 tcg ctg ctg ctg ccg cgc gag ctg aag gtg cag acg gtg gag aac gtc     1248
Ser Leu Leu Leu Pro Arg Glu Leu Lys Val Gln Thr Val Glu Asn Val
                405                 410                 415 gtc gac aac gag ctg gtg cgc gag gag ggc gtg tcg tgg gtg gtg ggg     1296
Val Asp Asn Glu Leu Val Arg Glu Glu Gly Val Ser Trp Val Val Gly
            420                 425                 430 gag tcg gac aac cag acg gcc agg ctg cgc acg ctg ggg atc acg atc     1344
Glu Ser Asp Asn Gln Thr Ala Arg Leu Arg Thr Leu Gly Ile Thr Ile
        435                 440                 445 gcc cgg gag acc aag gcg gcc ctg ctg gcc aac ggc tcg gtg acc gcg     1392
Ala Arg Glu Thr Lys Ala Ala Leu Leu Ala Asn Gly Ser Val Thr Ala
    450                 455                 460 gag gag gac cgc acg ctg cag acg gcg gcc gtc gtg ccg ttc gcg caa     1440
Glu Glu Asp Arg Thr Leu Gln Thr Ala Ala Val Val Pro Phe Ala Gln
465                 470                 475                 480 tcg ccg agc tcc aag ttc ttc gtg ctg acg gcc cag ctg gag ttc ccc     1488
```

-continued

```
                Ser Pro Ser Ser Lys Phe Phe Val Leu Thr Ala Gln Leu Glu Phe Pro
                                485                 490                 495 gcg agc gcg cgc tcg tcc ccg ctc cag tcc ggg ttc gaa atc ctg gcg           1536
Ala Ser Ala Arg Ser Ser Pro Leu Gln Ser Gly Phe Glu Ile Leu Ala
        500                 505                 510 tcg gag ctg gag cgc acg gcc atc tac tac cag ttc agc aac gag tcg           1584
Ser Glu Leu Glu Arg Thr Ala Ile Tyr Tyr Gln Phe Ser Asn Glu Ser
    515                 520                 525 ctg gtc gtc gac cgc agc cag act agt gcg gcg gcg ccc acg aac ccc           1632
Leu Val Val Asp Arg Ser Gln Thr Ser Ala Ala Ala Pro Thr Asn Pro
530                 535                 540 ggg ctg gat agc ttt act gag tcc ggc aag ttg cgg ttg ttc gac gtg           1680
Gly Leu Asp Ser Phe Thr Glu Ser Gly Lys Leu Arg Leu Phe Asp Val
545                 550                 555                 560 atc gag aac ggc cag gag cag gtc gag acg ttg gat ctc act gtc gtc           1728
Ile Glu Asn Gly Gln Glu Gln Val Glu Thr Leu Asp Leu Thr Val Val
                565                 570                 575 gtg gat aac gcg gtt gtc gag gtg tat gcc aac ggg cgc ttt gcg ttg           1776
Val Asp Asn Ala Val Val Glu Val Tyr Ala Asn Gly Arg Phe Ala Leu
            580                 585                 590 agc acc tgg gcg aga tcg tgg tac gac aac tcc acc cag atc cgc ttc           1824
Ser Thr Trp Ala Arg Ser Trp Tyr Asp Asn Ser Thr Gln Ile Arg Phe
        595                 600                 605 ttc cac aac ggc gag ggc gag gtg cag ttc agg aat gtc tcc gtg tcg           1872
Phe His Asn Gly Glu Gly Glu Val Gln Phe Arg Asn Val Ser Val Ser
    610                 615                 620 gag ggg ctc tat aac gcc tgg ccg gag aga aat                               1905
Glu Gly Leu Tyr Asn Ala Trp Pro Glu Arg Asn
625                 630                 635

<210> SEQ ID NO 2
<211> LENGTH: 635
<212> TYPE: PRT
<213> ORGANISM: Aspergillus niger

<400> SEQUENCE: 2

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
            35                  40                  45

Pro Ser Thr Gly Leu Phe His Val Gly Phe Leu His Asp Gly Asp Gly
        50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Phe Leu Pro Ile His Trp Ser Ile
        115                 120                 125

Pro Tyr Thr Arg Gly Ser Glu Thr Gln Ser Leu Ala Val Ala Arg Asp
    130                 135                 140

Gly Gly Arg Arg Phe Asp Lys Leu Asp Gln Gly Pro Val Ile Ala Asp
145                 150                 155                 160

His Pro Phe Ala Val Asp Val Thr Ala Phe Arg Asp Pro Phe Val Phe
                165                 170                 175
```

-continued

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
        210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Gly Ser Gly Leu Pro
        290                 295                 300

Ile Val Pro Gln Val Ser Ser Ile His Asp Met Leu Trp Ala Ala Gly
305                 310                 315                 320

Glu Val Gly Val Gly Ser Gln Glu Gly Ala Lys Val Glu Phe Ser
                325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ser Ala Val Ser Lys Thr Ser Gly
        355                 360                 365

Val Glu Val Asp Arg Tyr Val Ser Phe Val Trp Leu Thr Gly Asp Gln
        370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Glu Gly Val Ser Trp Val Val Gly
            420                 425                 430

Glu Ser Asp Asn Gln Thr Ala Arg Leu Arg Thr Leu Gly Ile Thr Ile
        435                 440                 445

Ala Arg Glu Thr Lys Ala Ala Leu Leu Ala Asn Gly Ser Val Thr Ala
450                 455                 460

Glu Glu Asp Arg Thr Leu Gln Thr Ala Ala Val Pro Phe Ala Gln
465                 470                 475                 480

Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
            500                 505                 510

Ser Glu Leu Glu Arg Thr Ala Ile Tyr Tyr Gln Phe Ser Asn Glu Ser
        515                 520                 525

Leu Val Val Asp Arg Ser Gln Thr Ser Ala Ala Pro Thr Asn Pro
530                 535                 540

Gly Leu Asp Ser Phe Thr Glu Ser Gly Lys Leu Arg Leu Phe Asp Val
545                 550                 555                 560

Ile Glu Asn Gly Gln Glu Gln Val Glu Thr Leu Asp Leu Thr Val Val
                565                 570                 575

Val Asp Asn Ala Val Val Glu Val Tyr Ala Asn Gly Arg Phe Ala Leu
            580                 585                 590

-continued

```
Ser Thr Trp Ala Arg Ser Trp Tyr Asp Asn Ser Thr Gln Ile Arg Phe
        595                 600                 605

Phe His Asn Gly Glu Gly Glu Val Gln Phe Arg Asn Val Ser Val Ser
    610                 615                 620

Glu Gly Leu Tyr Asn Ala Trp Pro Glu Arg Asn
625                 630                 635

<210> SEQ ID NO 3
<211> LENGTH: 1809
<212> TYPE: DNA
<213> ORGANISM: Penicillium roqueforti
<220> FEATURE:
<221> NAME/KEY: CDS
<222> LOCATION: (1)..(1809)

<400> SEQUENCE: 3 gtt gat ttc cat acc ccg att gac tat aac tcg gct ccg cca aac ctt      48
Val Asp Phe His Thr Pro Ile Asp Tyr Asn Ser Ala Pro Pro Asn Leu
1               5                   10                  15 tct acc ctg gca aac gca tct ctt ttc aag aca tgg aga ccc aga gcc      96
Ser Thr Leu Ala Asn Ala Ser Leu Phe Lys Thr Trp Arg Pro Arg Ala
            20                  25                  30 cat ctt ctc cct cca tct ggg aac ata ggc gac ccg tgc ggg cac tat     144
His Leu Leu Pro Pro Ser Gly Asn Ile Gly Asp Pro Cys Gly His Tyr
        35                  40                  45 acc gat ccc aag act ggt ctc ttc cac gtg ggt tgg ctt tac agt ggg     192
Thr Asp Pro Lys Thr Gly Leu Phe His Val Gly Trp Leu Tyr Ser Gly
    50                  55                  60 att tcg gga gcg aca acc gac gat ctc gtt acc tat aaa gac ctc aat     240
Ile Ser Gly Ala Thr Thr Asp Asp Leu Val Thr Tyr Lys Asp Leu Asn
65                  70                  75                  80 ccc gat gga gcc ccg tca att gtt gca gga gga aag aac gac cct ctt     288
Pro Asp Gly Ala Pro Ser Ile Val Ala Gly Gly Lys Asn Asp Pro Leu
                85                  90                  95 tct gtc ttc gat ggc tcg gtc att cca agc ggt ata gac ggc atg cca     336
Ser Val Phe Asp Gly Ser Val Ile Pro Ser Gly Ile Asp Gly Met Pro
            100                 105                 110 act ctt ctg tat acc tct gta tca tac ctc cca atc cac tgg tcc atc     384
Thr Leu Leu Tyr Thr Ser Val Ser Tyr Leu Pro Ile His Trp Ser Ile
        115                 120                 125 ccc tac acc cgg gga agc gag aca caa tcc ttg gcc gtt tcc tat gac     432
Pro Tyr Thr Arg Gly Ser Glu Thr Gln Ser Leu Ala Val Ser Tyr Asp
    130                 135                 140 ggt ggt cac aac ttc acc aag ctc aac caa ggg ccc gtg atc cct acg     480
Gly Gly His Asn Phe Thr Lys Leu Asn Gln Gly Pro Val Ile Pro Thr
145                 150                 155                 160 cct ccg ttt gct ctc aat gtc acc gct ttc cgt gac ccc tac gtt ttc     528
Pro Pro Phe Ala Leu Asn Val Thr Ala Phe Arg Asp Pro Tyr Val Phe
                165                 170                 175 caa agc cca att ctg gac aaa tct gtc aat agt acc caa gga aca tgg     576
Gln Ser Pro Ile Leu Asp Lys Ser Val Asn Ser Thr Gln Gly Thr Trp
            180                 185                 190 tat gtc gcc ata tct ggc ggt gtc cac ggt gtc gga cct tgt cag ttc     624
Tyr Val Ala Ile Ser Gly Gly Val His Gly Val Gly Pro Cys Gln Phe
        195                 200                 205 ctc tac cgt cag aac gac gca gat ttt caa tat tgg gaa tat ctc ggg     672
Leu Tyr Arg Gln Asn Asp Ala Asp Phe Gln Tyr Trp Glu Tyr Leu Gly
    210                 215                 220 caa tgg tgg aag gag ccc ctt aat acc act tgg gga aag ggt gac tgg     720
Gln Trp Trp Lys Glu Pro Leu Asn Thr Thr Trp Gly Lys Gly Asp Trp
225                 230                 235                 240
```

```
gcc ggg ggt tgg ggc ttc aac ttt gag gtt ggc aac gtc ttt agt ctg      768
Ala Gly Gly Trp Gly Phe Asn Phe Glu Val Gly Asn Val Phe Ser Leu
            245                 250                 255 aat gca gag ggg tat agt gaa gac ggc gag ata ttc ata acc ctc ggt      816
Asn Ala Glu Gly Tyr Ser Glu Asp Gly Glu Ile Phe Ile Thr Leu Gly
        260                 265                 270 gct gag ggt tcg gga ctt ccc atc gtt cct caa gtc tcc tct att cgc      864
Ala Glu Gly Ser Gly Leu Pro Ile Val Pro Gln Val Ser Ser Ile Arg
    275                 280                 285 gat atg ctg tgg gtg acc ggc aat gtc aca aat gac ggc tct gtc act      912
Asp Met Leu Trp Val Thr Gly Asn Val Thr Asn Asp Gly Ser Val Thr
290                 295                 300 ttc aag cca acc atg gcg ggt gtg ctt gac tgg ggc gtg tcg gca tat      960
Phe Lys Pro Thr Met Ala Gly Val Leu Asp Trp Gly Val Ser Ala Tyr
305                 310                 315                 320 gct gct gca ggc aag atc ttg ccg gcc agc tct cag gca tcc aca aag     1008
Ala Ala Ala Gly Lys Ile Leu Pro Ala Ser Ser Gln Ala Ser Thr Lys
                325                 330                 335 agc ggt gcc ccc gat cgg ttc att tcc tat gtc tgg ctc act gga gat     1056
Ser Gly Ala Pro Asp Arg Phe Ile Ser Tyr Val Trp Leu Thr Gly Asp
            340                 345                 350 cta ttc gag caa gtg aaa gga ttc cct acc gct caa caa aac tgg acc     1104
Leu Phe Glu Gln Val Lys Gly Phe Pro Thr Ala Gln Gln Asn Trp Thr
        355                 360                 365 ggg gcc ctc tta ctg ccg cga gag ctg aat gtc cgc act atc tct aac     1152
Gly Ala Leu Leu Leu Pro Arg Glu Leu Asn Val Arg Thr Ile Ser Asn
    370                 375                 380 gtg gtg gat aac gaa ctt tcg cgt gag tcc ttg aca tcg tgg cgc gtg     1200
Val Val Asp Asn Glu Leu Ser Arg Glu Ser Leu Thr Ser Trp Arg Val
385                 390                 395                 400 gcc cgc gaa gac tct ggt cag atc gac ctt gaa aca atg gga atc tca     1248
Ala Arg Glu Asp Ser Gly Gln Ile Asp Leu Glu Thr Met Gly Ile Ser
                405                 410                 415 att tcc agg gag act tac agc gct ctc aca tcc ggc tca tct ttt gtc     1296
Ile Ser Arg Glu Thr Tyr Ser Ala Leu Thr Ser Gly Ser Ser Phe Val
            420                 425                 430 gag tct ggt aaa acg ttg tcg aat gct gga gca gtg ccc ttc aat acc     1344
Glu Ser Gly Lys Thr Leu Ser Asn Ala Gly Ala Val Pro Phe Asn Thr
        435                 440                 445 tca ccc tca agc aag ttc ttc gtg ctg aca gca aat ata tct ttc ccg     1392
Ser Pro Ser Ser Lys Phe Phe Val Leu Thr Ala Asn Ile Ser Phe Pro
    450                 455                 460 acc tct gcc cgt gac tct ggc atc cag gct ggt ttc cag gtt tta tcc     1440
Thr Ser Ala Arg Asp Ser Gly Ile Gln Ala Gly Phe Gln Val Leu Ser
465                 470                 475                 480 tct agt ctt gag tct aca act atc tac tac caa ttc tcc aac gag tcc     1488
Ser Ser Leu Glu Ser Thr Thr Ile Tyr Tyr Gln Phe Ser Asn Glu Ser
                485                 490                 495 atc atc gtc gac cgc agc aac acg agt gct gcg gcg aga aca act gct     1536
Ile Ile Val Asp Arg Ser Asn Thr Ser Ala Ala Ala Arg Thr Thr Ala
            500                 505                 510 ggg atc ctc agt gat aac gag gcg gga cgt ctg cgc ctc ttc gac gtg     1584
Gly Ile Leu Ser Asp Asn Glu Ala Gly Arg Leu Arg Leu Phe Asp Val
        515                 520                 525 ttg cga aat gga aaa gaa cag gtt gaa act ttg gag ctc act atc gtg     1632
Leu Arg Asn Gly Lys Glu Gln Val Glu Thr Leu Glu Leu Thr Ile Val
    530                 535                 540 gtg gat aat agt gta ctg gaa gta tat gcc aat gga cgc ttt gct cta     1680
Val Asp Asn Ser Val Leu Glu Val Tyr Ala Asn Gly Arg Phe Ala Leu
```

```
                545                 550                 555                 560
ggc  act  tgg  gct  cgg  tct  tgg  tac  gcc  aac  tcg  act  aaa  att  aac  ttc       1728
Gly  Thr  Trp  Ala  Arg  Ser  Trp  Tyr  Ala  Asn  Ser  Thr  Lys  Ile  Asn  Phe
                    565                      570                      575 ttc  cat  aac  ggc  gtg  gga  gaa  gcg  aca  ttc  gaa  gat  gtg  acg  gtc  ttt       1776
Phe  His  Asn  Gly  Val  Gly  Glu  Ala  Thr  Phe  Glu  Asp  Val  Thr  Val  Phe
               580                      585                      590 gaa  gga  ctg  tat  gat  gcc  tgg  cca  caa  agg  aag                                 1809
Glu  Gly  Leu  Tyr  Asp  Ala  Trp  Pro  Gln  Arg  Lys
          595                      600

<210> SEQ ID NO 4
<211> LENGTH: 603
<212> TYPE: PRT
<213> ORGANISM: Penicillium roqueforti

<400> SEQUENCE: 4
```

Val Asp Phe His Thr Pro Ile Asp Tyr Asn Ser Ala Pro Pro Asn Leu
1               5                   10                  15

Ser Thr Leu Ala Asn Ala Ser Leu Phe Lys Thr Trp Arg Pro Arg Ala
            20                  25                  30

His Leu Leu Pro Pro Ser Gly Asn Ile Gly Asp Pro Cys Gly His Tyr
        35                  40                  45

Thr Asp Pro Lys Thr Gly Leu Phe His Val Gly Trp Leu Tyr Ser Gly
    50                  55                  60

Ile Ser Gly Ala Thr Thr Asp Asp Leu Val Thr Tyr Lys Asp Leu Asn
65                  70                  75                  80

Pro Asp Gly Ala Pro Ser Ile Val Ala Gly Lys Asn Asp Pro Leu
                85                  90                  95

Ser Val Phe Asp Gly Ser Val Ile Pro Ser Gly Ile Asp Gly Met Pro
            100                 105                 110

Thr Leu Leu Tyr Thr Ser Val Ser Tyr Leu Pro Ile His Trp Ser Ile
        115                 120                 125

Pro Tyr Thr Arg Gly Ser Glu Thr Gln Ser Leu Ala Val Ser Tyr Asp
    130                 135                 140

Gly Gly His Asn Phe Thr Lys Leu Asn Gln Gly Pro Val Ile Pro Thr
145                 150                 155                 160

Pro Pro Phe Ala Leu Asn Val Thr Ala Phe Arg Asp Pro Tyr Val Phe
                165                 170                 175

Gln Ser Pro Ile Leu Asp Lys Ser Val Asn Ser Thr Gln Gly Thr Trp
            180                 185                 190

Tyr Val Ala Ile Ser Gly Gly Val His Gly Val Gly Pro Cys Gln Phe
        195                 200                 205

Leu Tyr Arg Gln Asn Asp Ala Asp Phe Gln Tyr Trp Glu Tyr Leu Gly
    210                 215                 220

Gln Trp Trp Lys Glu Pro Leu Asn Thr Thr Trp Gly Lys Gly Asp Trp
225                 230                 235                 240

Ala Gly Gly Trp Gly Phe Asn Phe Glu Val Gly Asn Val Phe Ser Leu
                245                 250                 255

Asn Ala Glu Gly Tyr Ser Glu Asp Gly Glu Ile Phe Ile Thr Leu Gly
            260                 265                 270

Ala Glu Gly Ser Gly Leu Pro Ile Val Pro Gln Val Ser Ser Ile Arg
        275                 280                 285

Asp Met Leu Trp Val Thr Gly Asn Val Thr Asn Asp Gly Ser Val Thr
    290                 295                 300

```
Phe Lys Pro Thr Met Ala Gly Val Leu Asp Trp Gly Val Ser Ala Tyr
305                 310                 315                 320
Ala Ala Ala Gly Lys Ile Leu Pro Ala Ser Ser Gln Ala Ser Thr Lys
                325                 330                 335
Ser Gly Ala Pro Asp Arg Phe Ile Ser Tyr Val Trp Leu Thr Gly Asp
            340                 345                 350
Leu Phe Glu Gln Val Lys Gly Phe Pro Thr Ala Gln Gln Asn Trp Thr
        355                 360                 365
Gly Ala Leu Leu Leu Pro Arg Glu Leu Asn Val Arg Thr Ile Ser Asn
    370                 375                 380
Val Val Asp Asn Glu Leu Ser Arg Glu Ser Leu Thr Ser Trp Arg Val
385                 390                 395                 400
Ala Arg Glu Asp Ser Gly Gln Ile Asp Leu Glu Thr Met Gly Ile Ser
                405                 410                 415
Ile Ser Arg Glu Thr Tyr Ser Ala Leu Thr Ser Gly Ser Ser Phe Val
            420                 425                 430
Glu Ser Gly Lys Thr Leu Ser Asn Ala Gly Ala Val Pro Phe Asn Thr
        435                 440                 445
Ser Pro Ser Ser Lys Phe Phe Val Leu Thr Ala Asn Ile Ser Phe Pro
    450                 455                 460
Thr Ser Ala Arg Asp Ser Gly Ile Gln Ala Gly Phe Gln Val Leu Ser
465                 470                 475                 480
Ser Ser Leu Glu Ser Thr Thr Ile Tyr Tyr Gln Phe Ser Asn Glu Ser
                485                 490                 495
Ile Ile Val Asp Arg Ser Asn Thr Ser Ala Ala Arg Thr Thr Ala
            500                 505                 510
Gly Ile Leu Ser Asp Asn Glu Ala Gly Arg Leu Arg Leu Phe Asp Val
        515                 520                 525
Leu Arg Asn Gly Lys Glu Gln Val Glu Thr Leu Glu Leu Thr Ile Val
    530                 535                 540
Val Asp Asn Ser Val Leu Glu Val Tyr Ala Asn Gly Arg Phe Ala Leu
545                 550                 555                 560
Gly Thr Trp Ala Arg Ser Trp Tyr Ala Asn Ser Thr Lys Ile Asn Phe
                565                 570                 575
Phe His Asn Gly Val Gly Glu Ala Thr Phe Glu Asp Val Thr Val Phe
            580                 585                 590
Glu Gly Leu Tyr Asp Ala Trp Pro Gln Arg Lys
        595                 600

<210> SEQ ID NO 5
<211> LENGTH: 1839
<212> TYPE: DNA
<213> ORGANISM: Scopulariopsis brevicaulis
<220> FEATURE:
<221> NAME/KEY: CDS
<222> LOCATION: (1)..(1839)

<400> SEQUENCE: 5 caa cct acg tct ctg tca atc gac aat tcc acg tat cct tct atc gac    48
Gln Pro Thr Ser Leu Ser Ile Asp Asn Ser Thr Tyr Pro Ser Ile Asp
1               5                   10                  15 tac aac tcc gcc cct cca aac ctc tcg act ctt gcc aac aac agc ctc    96
Tyr Asn Ser Ala Pro Pro Asn Leu Ser Thr Leu Ala Asn Asn Ser Leu
            20                  25                  30 ttc gag aca tgg agg ccg agg gca cac gtc ctt ccg ccc cag aac cag   144
Phe Glu Thr Trp Arg Pro Arg Ala His Val Leu Pro Pro Gln Asn Gln
        35                  40                  45
```

```
atc ggc gat ccg tgt atg cac tac acc gac ccc gag aca gga atc ttc      192
Ile Gly Asp Pro Cys Met His Tyr Thr Asp Pro Glu Thr Gly Ile Phe
 50                  55                  60 cac gtc ggc tgg ctg tac aac ggc aat ggc gct tcc ggc gcc acg acc      240
His Val Gly Trp Leu Tyr Asn Gly Asn Gly Ala Ser Gly Ala Thr Thr
 65                  70                  75                  80 gag gat ctc gtc acc tat cag gat ctc aac ccc gac gga gcg cag atg      288
Glu Asp Leu Val Thr Tyr Gln Asp Leu Asn Pro Asp Gly Ala Gln Met
                 85                  90                  95 atc ctt ccg ggt ggt gtg aat gac ccc att gct gtc ttt gac ggc gcg      336
Ile Leu Pro Gly Gly Val Asn Asp Pro Ile Ala Val Phe Asp Gly Ala
            100                 105                 110 gtt att ccc agt ggc att gat ggg aaa ccc acc atg atg tat acc tcg      384
Val Ile Pro Ser Gly Ile Asp Gly Lys Pro Thr Met Met Tyr Thr Ser
        115                 120                 125 gtg tca tac atg ccc atc tcc tgg agc atc gct tac acc agg gga agc      432
Val Ser Tyr Met Pro Ile Ser Trp Ser Ile Ala Tyr Thr Arg Gly Ser
130                 135                 140 gag acc cac tct ctc gca gtg tcg tcc gac ggc ggt aag aac ttc acc      480
Glu Thr His Ser Leu Ala Val Ser Ser Asp Gly Gly Lys Asn Phe Thr
145                 150                 155                 160 aag ctg gtg cag ggc ccc gtc att cct tcg cct ccc ttc ggc gcc aac      528
Lys Leu Val Gln Gly Pro Val Ile Pro Ser Pro Pro Phe Gly Ala Asn
                165                 170                 175 gtg acc agc tgg cgt gac ccc ttc ctg ttc caa aac ccc cag ttc gac      576
Val Thr Ser Trp Arg Asp Pro Phe Leu Phe Gln Asn Pro Gln Phe Asp
            180                 185                 190 tct ctc ctc gaa agc gag aac ggc acg tgg tac acc gtt atc tct ggt      624
Ser Leu Leu Glu Ser Glu Asn Gly Thr Trp Tyr Thr Val Ile Ser Gly
        195                 200                 205 ggc atc cac ggt gac ggc ccc tcc gcg ttc ctc tac cgt cag cac gac      672
Gly Ile His Gly Asp Gly Pro Ser Ala Phe Leu Tyr Arg Gln His Asp
210                 215                 220 ccc gac ttc cag tac tgg gag tac ctt gga ccg tgg tgg aac gag gaa      720
Pro Asp Phe Gln Tyr Trp Glu Tyr Leu Gly Pro Trp Trp Asn Glu Glu
225                 230                 235                 240 ggg aac tcg acc tgg ggc agc ggt gac tgg gct ggc cgg tgg ggc tac      768
Gly Asn Ser Thr Trp Gly Ser Gly Asp Trp Ala Gly Arg Trp Gly Tyr
                245                 250                 255 aac ttc gag gtc atc aac att gtc ggt ctt gac gat gat ggc tac aac      816
Asn Phe Glu Val Ile Asn Ile Val Gly Leu Asp Asp Asp Gly Tyr Asn
            260                 265                 270 ccc gac ggt gaa atc ttt gcc acg gta ggt acc gaa tgg tcg ttt gac      864
Pro Asp Gly Glu Ile Phe Ala Thr Val Gly Thr Glu Trp Ser Phe Asp
        275                 280                 285 ccc atc aaa ccg cag gcc tcg gac aac agg gag atg ctc tgg gcc gcg      912
Pro Ile Lys Pro Gln Ala Ser Asp Asn Arg Glu Met Leu Trp Ala Ala
290                 295                 300 ggc aac atg act ctc gag gac ggc gat atc aag ttc acg cca agc atg      960
Gly Asn Met Thr Leu Glu Asp Gly Asp Ile Lys Phe Thr Pro Ser Met
305                 310                 315                 320 gcg ggc tac ctc gac tgg ggt cta tcg gcg tat gcc gcc gct ggc aag     1008
Ala Gly Tyr Leu Asp Trp Gly Leu Ser Ala Tyr Ala Ala Ala Gly Lys
                325                 330                 335 gag ctg ccc gct tct tca aag cct tcg cag aag agc ggt gcg ccg gac     1056
Glu Leu Pro Ala Ser Ser Lys Pro Ser Gln Lys Ser Gly Ala Pro Asp
            340                 345                 350 cgg ttc gtg tcg tac ctg tgg ctc acc ggt gac tac ttc gag ggc cac     1104
Arg Phe Val Ser Tyr Leu Trp Leu Thr Gly Asp Tyr Phe Glu Gly His
```

```
                    355                 360                 365
gac ttc ccc acc ccg cag cag aat tgg acc ggc tcg ctt ttg ctt ccg      1152
Asp Phe Pro Thr Pro Gln Gln Asn Trp Thr Gly Ser Leu Leu Leu Pro
    370                 375                 380 cgt gag ctg agc gtc ggg acg att ccc aac gtt gtc gac aac gag ctt      1200
Arg Glu Leu Ser Val Gly Thr Ile Pro Asn Val Val Asp Asn Glu Leu
385                 390                 395                 400 gct cgc gag acg ggc tct tgg agg gtt ggc acc aac gac act ggc gtg      1248
Ala Arg Glu Thr Gly Ser Trp Arg Val Gly Thr Asn Asp Thr Gly Val
                405                 410                 415 ctt gag ctg gtc act ctg aag cag gag att gct cgc gag acg ctg gct      1296
Leu Glu Leu Val Thr Leu Lys Gln Glu Ile Ala Arg Glu Thr Leu Ala
            420                 425                 430 gaa atg acc agc ggc aac tcc ttc acc gag gcg agc agg aat gtc agc      1344
Glu Met Thr Ser Gly Asn Ser Phe Thr Glu Ala Ser Arg Asn Val Ser
        435                 440                 445 tcg ccc gga tct acc gcc ttc cag cag tcc ctg gat tcc aag ttc ttc      1392
Ser Pro Gly Ser Thr Ala Phe Gln Gln Ser Leu Asp Ser Lys Phe Phe
    450                 455                 460 gtc ctg acc gcc tcg ctc tcc ttc cct tcg tcg gct cgc gac tcc gac      1440
Val Leu Thr Ala Ser Leu Ser Phe Pro Ser Ser Ala Arg Asp Ser Asp
465                 470                 475                 480 ctc aag gct ggt ttc gag atc ctg tcg tcc gag ttt gag tcg acc acg      1488
Leu Lys Ala Gly Phe Glu Ile Leu Ser Ser Glu Phe Glu Ser Thr Thr
                485                 490                 495 gtc tac tac cag ttt tcc aac gag tcc atc atc att gac cgg agc aac      1536
Val Tyr Tyr Gln Phe Ser Asn Glu Ser Ile Ile Ile Asp Arg Ser Asn
            500                 505                 510 tcg agt gct gcc gcc ttg act acc gat gga atc gac acc cgc aac gag      1584
Ser Ser Ala Ala Ala Leu Thr Thr Asp Gly Ile Asp Thr Arg Asn Glu
        515                 520                 525 ttt ggc aag atg cgc ctg ttt gat gtt gtc gag ggt gac cag gag cgt      1632
Phe Gly Lys Met Arg Leu Phe Asp Val Val Glu Gly Asp Gln Glu Arg
    530                 535                 540 atc gag acg ctc gat ctc act att gtg gtt gat aac tcg atc gtt gag      1680
Ile Glu Thr Leu Asp Leu Thr Ile Val Val Asp Asn Ser Ile Val Glu
545                 550                 555                 560 gtt cat gcc aac ggg cga ttc gct ctg agc act tgg gtt cgt tcg tgg      1728
Val His Ala Asn Gly Arg Phe Ala Leu Ser Thr Trp Val Arg Ser Trp
                565                 570                 575 tac gag tcg tcc aag gac atc aag ttc ttc cac gat ggc gac agc acg      1776
Tyr Glu Ser Ser Lys Asp Ile Lys Phe Phe His Asp Gly Asp Ser Thr
            580                 585                 590 gtt cag ttc tcg aac atc acc gtc tac gag gga ctg ttt gac gcc tgg      1824
Val Gln Phe Ser Asn Ile Thr Val Tyr Glu Gly Leu Phe Asp Ala Trp
        595                 600                 605 ccg gag cgg gcc agg                                                  1839
Pro Glu Arg Ala Arg
    610

<210> SEQ ID NO 6
<211> LENGTH: 613
<212> TYPE: PRT
<213> ORGANISM: Scopulariopsis brevicaulis

<400> SEQUENCE: 6

Gln Pro Thr Ser Leu Ser Ile Asp Asn Ser Thr Tyr Pro Ser Ile Asp
1               5                   10                  15

Tyr Asn Ser Ala Pro Pro Asn Leu Ser Thr Leu Ala Asn Asn Ser Leu
            20                  25                  30
```

-continued

```
Phe Glu Thr Trp Arg Pro Arg Ala His Val Leu Pro Pro Gln Asn Gln
         35                  40                  45

Ile Gly Asp Pro Cys Met His Tyr Thr Asp Pro Glu Thr Gly Ile Phe
 50                  55                  60

His Val Gly Trp Leu Tyr Asn Gly Asn Gly Ala Ser Gly Ala Thr Thr
 65                  70                  75                  80

Glu Asp Leu Val Thr Tyr Gln Asp Leu Asn Pro Asp Gly Ala Gln Met
                 85                  90                  95

Ile Leu Pro Gly Gly Val Asn Asp Pro Ile Ala Val Phe Asp Gly Ala
                100                 105                 110

Val Ile Pro Ser Gly Ile Asp Gly Lys Pro Thr Met Met Tyr Thr Ser
            115                 120                 125

Val Ser Tyr Met Pro Ile Ser Trp Ser Ile Ala Tyr Thr Arg Gly Ser
        130                 135                 140

Glu Thr His Ser Leu Ala Val Ser Ser Asp Gly Gly Lys Asn Phe Thr
145                 150                 155                 160

Lys Leu Val Gln Gly Pro Val Ile Pro Ser Pro Phe Gly Ala Asn
                165                 170                 175

Val Thr Ser Trp Arg Asp Pro Phe Leu Phe Gln Asn Pro Gln Phe Asp
            180                 185                 190

Ser Leu Leu Glu Ser Glu Asn Gly Thr Trp Tyr Thr Val Ile Ser Gly
        195                 200                 205

Gly Ile His Gly Asp Gly Pro Ser Ala Phe Leu Tyr Arg Gln His Asp
    210                 215                 220

Pro Asp Phe Gln Tyr Trp Glu Tyr Leu Gly Pro Trp Trp Asn Glu Glu
225                 230                 235                 240

Gly Asn Ser Thr Trp Gly Ser Gly Asp Trp Ala Gly Arg Trp Gly Tyr
                245                 250                 255

Asn Phe Glu Val Ile Asn Ile Val Gly Leu Asp Asp Asp Gly Tyr Asn
            260                 265                 270

Pro Asp Gly Glu Ile Phe Ala Thr Val Gly Thr Glu Trp Ser Phe Asp
        275                 280                 285

Pro Ile Lys Pro Gln Ala Ser Asp Asn Arg Glu Met Leu Trp Ala Ala
290                 295                 300

Gly Asn Met Thr Leu Glu Asp Gly Asp Ile Lys Phe Thr Pro Ser Met
305                 310                 315                 320

Ala Gly Tyr Leu Asp Trp Gly Leu Ser Ala Tyr Ala Ala Ala Gly Lys
                325                 330                 335

Glu Leu Pro Ala Ser Ser Lys Pro Ser Gln Lys Ser Gly Ala Pro Asp
            340                 345                 350

Arg Phe Val Ser Tyr Leu Trp Leu Thr Gly Asp Tyr Phe Glu Gly His
        355                 360                 365

Asp Phe Pro Thr Pro Gln Gln Asn Trp Thr Gly Ser Leu Leu Leu Pro
    370                 375                 380

Arg Glu Leu Ser Val Gly Thr Ile Pro Asn Val Val Asp Asn Glu Leu
385                 390                 395                 400

Ala Arg Glu Thr Gly Ser Trp Arg Val Gly Thr Asn Asp Thr Gly Val
                405                 410                 415

Leu Glu Leu Val Thr Leu Lys Gln Glu Ile Ala Arg Glu Thr Leu Ala
            420                 425                 430

Glu Met Thr Ser Gly Asn Ser Phe Thr Glu Ala Ser Arg Asn Val Ser
        435                 440                 445
```

```
Ser Pro Gly Ser Thr Ala Phe Gln Gln Ser Leu Asp Ser Lys Phe Phe
    450                 455                 460

Val Leu Thr Ala Ser Leu Ser Phe Pro Ser Ser Ala Arg Asp Ser Asp
465                 470                 475                 480

Leu Lys Ala Gly Phe Glu Ile Leu Ser Ser Glu Phe Glu Ser Thr Thr
                485                 490                 495

Val Tyr Tyr Gln Phe Ser Asn Glu Ser Ile Ile Ile Asp Arg Ser Asn
            500                 505                 510

Ser Ser Ala Ala Ala Leu Thr Thr Asp Gly Ile Asp Thr Arg Asn Glu
        515                 520                 525

Phe Gly Lys Met Arg Leu Phe Asp Val Val Glu Gly Asp Gln Glu Arg
    530                 535                 540

Ile Glu Thr Leu Asp Leu Thr Ile Val Val Asp Asn Ser Ile Val Glu
545                 550                 555                 560

Val His Ala Asn Gly Arg Phe Ala Leu Ser Thr Trp Val Arg Ser Trp
                565                 570                 575

Tyr Glu Ser Ser Lys Asp Ile Lys Phe Phe His Asp Gly Asp Ser Thr
            580                 585                 590

Val Gln Phe Ser Asn Ile Thr Val Tyr Glu Gly Leu Phe Asp Ala Trp
        595                 600                 605

Pro Glu Arg Ala Arg
    610

<210> SEQ ID NO 7
<211> LENGTH: 27
<212> TYPE: DNA
<213> ORGANISM: Artificial Sequence
<220> FEATURE:
<223> OTHER INFORMATION: Oligonucleotide

<400> SEQUENCE: 7
gcgaattcat gaagctcacc actacca                                      27

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide

<400> SEQUENCE: 8
gcggatcccg gtcaatttct ct                                           22

<210> SEQ ID NO 9
<211> LENGTH: 9
<212> TYPE: DNA
<213> ORGANISM: Aspergillus niger
<220> FEATURE:
<221> NAME/KEY: CDS
<222> LOCATION: (1)..(9)

<400> SEQUENCE: 9 gac gag gac                                                         9
Asp Glu Asp
1

<210> SEQ ID NO 10
<211> LENGTH: 9
<212> TYPE: DNA
<213> ORGANISM: Aspergillus niger
<220> FEATURE:
<221> NAME/KEY: CDS
```

```
<222> LOCATION: (1)..(9)

<400> SEQUENCE: 10 ttc atg ccc                                                          9
Phe Met Pro
1

<210> SEQ ID NO 11
<211> LENGTH: 9
<212> TYPE: DNA
<213> ORGANISM: Aspergillus niger
<220> FEATURE:
<221> NAME/KEY: CDS
<222> LOCATION: (1)..(9)

<400> SEQUENCE: 11 tcc aac ccc                                                          9
Ser Asn Pro
1

<210> SEQ ID NO 12
<211> LENGTH: 9
<212> TYPE: DNA
<213> ORGANISM: Aspergillus niger
<220> FEATURE:
<221> NAME/KEY: CDS
<222> LOCATION: (1)..(9)

<400> SEQUENCE: 12 gcc ttc gac                                                          9
Ala Phe Asp
1

<210> SEQ ID NO 13
<211> LENGTH: 9
<212> TYPE: DNA
<213> ORGANISM: Aspergillus niger
<220> FEATURE:
<221> NAME/KEY: CDS
<222> LOCATION: (1)..(9)

<400> SEQUENCE: 13 gtg tac ggc                                                          9
Val Tyr Gly
1

<210> SEQ ID NO 14
<211> LENGTH: 9
<212> TYPE: DNA
<213> ORGANISM: Aspergillus niger
<220> FEATURE:
<221> NAME/KEY: CDS
<222> LOCATION: (1)..(9)

<400> SEQUENCE: 14 gcc ctg cag                                                          9
Ala Leu Gln
1

<210> SEQ ID NO 15
<211> LENGTH: 9
<212> TYPE: DNA
<213> ORGANISM: Aspergillus niger
<220> FEATURE:
<221> NAME/KEY: CDS
<222> LOCATION: (1)..(9)

<400> SEQUENCE: 15
```

```
ttt tcg gag                                                              9
Phe Ser Glu
  1

<210> SEQ ID NO 16
<211> LENGTH: 9
<212> TYPE: DNA
<213> ORGANISM: Aspergillus niger
<220> FEATURE:
<221> NAME/KEY: CDS
<222> LOCATION: (1)..(9)

<400> SEQUENCE: 16 atc gac gac                                                              9
Ile Asp Asp
  1

<210> SEQ ID NO 17
<211> LENGTH: 9
<212> TYPE: DNA
<213> ORGANISM: Aspergillus niger
<220> FEATURE:
<221> NAME/KEY: CDS
<222> LOCATION: (1)..(9)

<400> SEQUENCE: 17 ttg atg ggc                                                              9
Leu Met Gly
  1

<210> SEQ ID NO 18
<211> LENGTH: 9
<212> TYPE: DNA
<213> ORGANISM: Aspergillus niger
<220> FEATURE:
<221> NAME/KEY: CDS
<222> LOCATION: (1)..(9)

<400> SEQUENCE: 18 gtc tgc ttg                                                              9
Val Cys Leu
  1
```